(12) United States Patent
Sayama (10) Patent No.: US 7,252,658 B2
(45) Date of Patent: Aug. 7, 2007

(54) OPEN-TYPE DISPOSABLE DIAPER

(75) Inventor: Yasushi Sayama, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 179 days.

(21) Appl. No.: 10/214,222

(22) Filed: Aug. 7, 2002

(65) Prior Publication Data

US 2003/0032933 A1   Feb. 13, 2003

(51) Int. Cl.
*A61F 13/15* (2006.01)

(52) U.S. Cl. ............... 604/396; 604/398; 604/386; 604/391; 604/385.24; 604/385.27

(58) Field of Classification Search ............... 604/396, 604/398, 386, 387, 385.04, 385.24, 385.27, 604/391
See application file for complete search history.

(56) References Cited

U.S. PATENT DOCUMENTS

| 4,753,650 | A |   | 6/1988 | Williams |
| 4,850,988 | A |   | 7/1989 | Aledo et al. |
| 4,850,992 | A |   | 7/1989 | Amaral et al. |
| 5,069,678 | A | * | 12/1991 | Yamamoto et al. .... 604/385.21 |
| 5,370,634 | A | * | 12/1994 | Ando et al. ............ 604/385.21 |
| H001674 | H | * | 8/1997 | Ames et al. ................. 604/389 |
| 5,899,895 | A | * | 5/1999 | Robles et al. .......... 604/385.29 |
| 6,004,306 | A |   | 12/1999 | Dakin et al. |

FOREIGN PATENT DOCUMENTS

| GB | 2 080 093 | 2/1982 |
| JP | 7-227403 | 8/1995 |
| WO | WO 98/35642 | 8/1998 |

* cited by examiner

*Primary Examiner*—Jacqueline F Stephens
(74) *Attorney, Agent, or Firm*—Butzel Long (57) ABSTRACT

A diaper has two pairs of means adapted to connect transversely opposite side edge portions of a front waist region and a rear waist region. These connecting means are elastically stretchable in a transverse direction of the diaper and the connecting means lying at a lower portion of the side edge portions have a stretch stress a great as that of the connecting means lying at a upper portion of the side edge portions.

8 Claims, 6 Drawing Sheets

OPEN-TYPE DISPOSABLE DIAPER

BACKGROUND OF THE INVENTION

This invention relates to an open-type disposable diaper.

Japanese Patent Publication No. 1995-227403A discloses an open-type disposable diaper. In the diaper disclosed therein, a pair of upper and lower tape fasteners extend outward from transversely opposite side edge portions in a rear waist region of the diaper in parallel to each other in a waist-surrounding direction. These tape fasteners are attached to a backsheet by means of elastically stretchable portions thereof. These tape fasteners are adapted to be anchored on a front waist region, stretching these stretchable portions in the waist-surrounding direction. Of a pair of upper and lower tape fasteners, the upper tape fastener serves to put the diaper in close contact primarily with wearer's body and the lower tape fastener serves to put the diaper in close contact primarily with wearer's thighs.

A pair of upper and lower tape fasteners in the diaper of well known art as disclosed in the above-cited Publication is formed with the elastic portions which are substantially identical. Therefore, while these tape fasteners are able to put the diaper on a wearer's body in close contact with the wearer's torso and thighs tightly or gently, it is difficult for such a diaper to put the diaper in close contact tightly with wearer's thighs and thereby to eliminate an anxiety that bodily discharges might leak beyond thigh-surrounding peripheral edged and at the same time to put the diaper in close contact gently with the wearer's body without disturbing the wearer's abdominal breathing. With the stretchable portions having a relatively great stretch stress, if these stretchable portions are pulled intentionally with a relatively weak force in order to put the diaper in close contact gently with the wearer's body, a gap would be formed between the diaper and the wearer's body through which bodily discharges may leak.

SUMMARY OF THE INVENTION

An object of this invention is to improve an open-type disposable diaper having a pair of connecting means, such as a pair of tape fasteners, which is lying at transversely opposite side edge portions and extending in parallel to each other so that the diaper may be put in close contact with the wearer's torso and thighs with an appropriate fitness by such a connecting means.

According to this invention, there is provided an open-type disposable diaper comprising, in a longitudinal direction, a front waist region, a rear waist region and a crotch region extending between these waist regions and contoured by transversely opposite side edge portions extending in the longitudinal direction and front and rear end portions extending in a transverse direction of the diaper orthogonal to the longitudinal direction wherein the diaper further includes two pairs of connecting means extending in parallel to each other in the transverse direction and serving to connect the side edge portions of the front and rear waist regions.

This invention further comprises the two pairs of connecting means which are elastically stretchable in the transverse direction and the one pair of the connecting means lying at a lower portion of the side edge portions have a stretch stress greater than that of the connecting means lying at an upper portion of the side edge portions.

According to one preferred embodiment of this invention, the connecting means lying at the lower portion have a stress 1.2-2 times as great as that of the connecting means lying at the upper portion when these connecting means are stretched by 30%, respectively. According to another preferred embodiment of this invention, the connecting means lying at the upper portion of the side edge portions extend outward from the side edge portions in the front waist region and are adapted to be anchored on the rear waist region in such a manner to be released and the connecting means lying at the lower portion of the side edge portions extend outward from the side edge portions in the rear waist region and are adapted to be anchored on the front waist region in such a manner to be released.

DETAILED DESCRIPTION OF THE PREFERRED EMBODIMENTS

Details of the disposable diaper according to this invention will be more fully understood from the description given hereunder in reference to the accompanying drawings.

Figure 1:
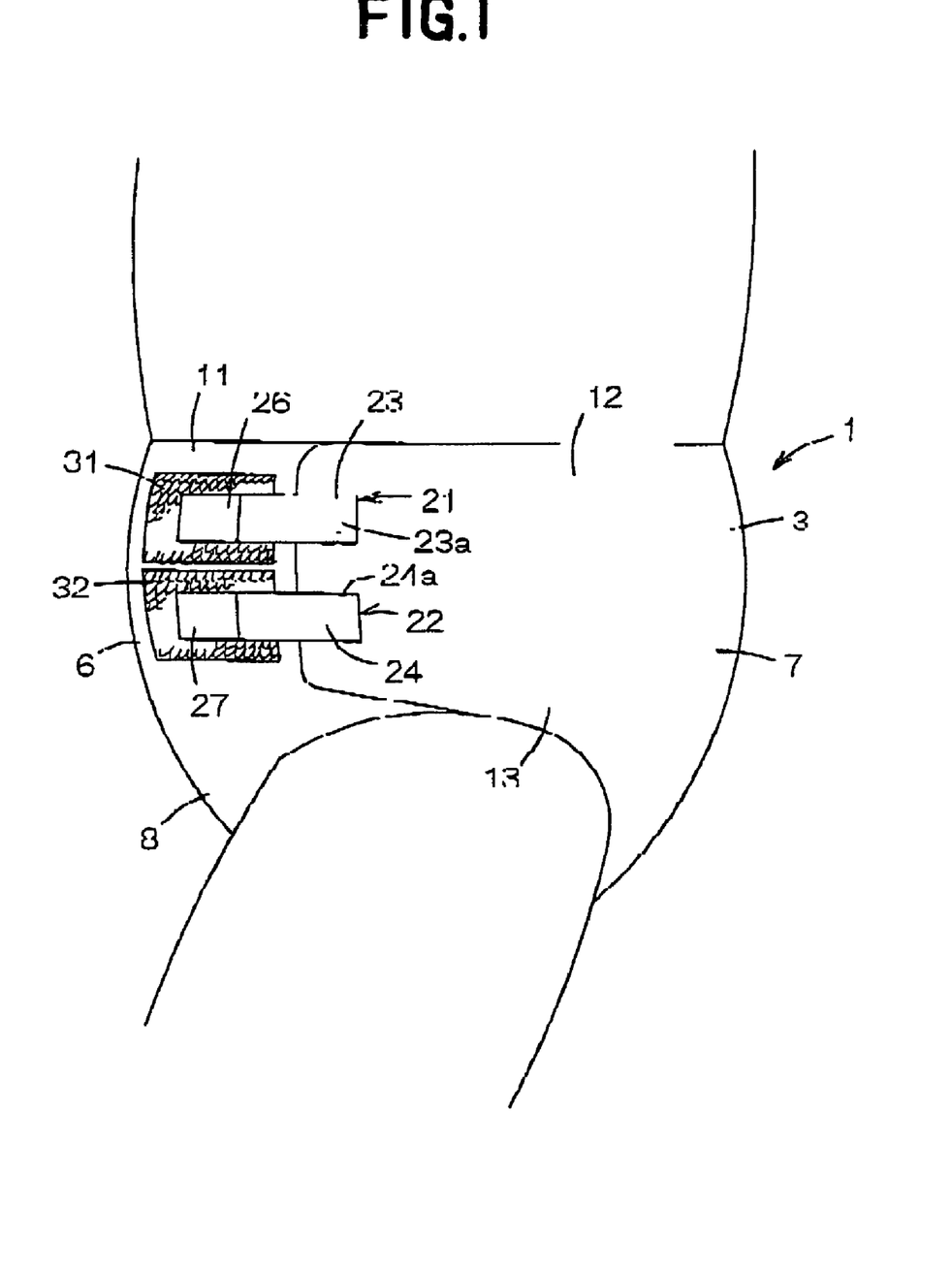
FIG. 1 is a side view showing a disposable diaper as put on a wearer's body.
Figure 2:
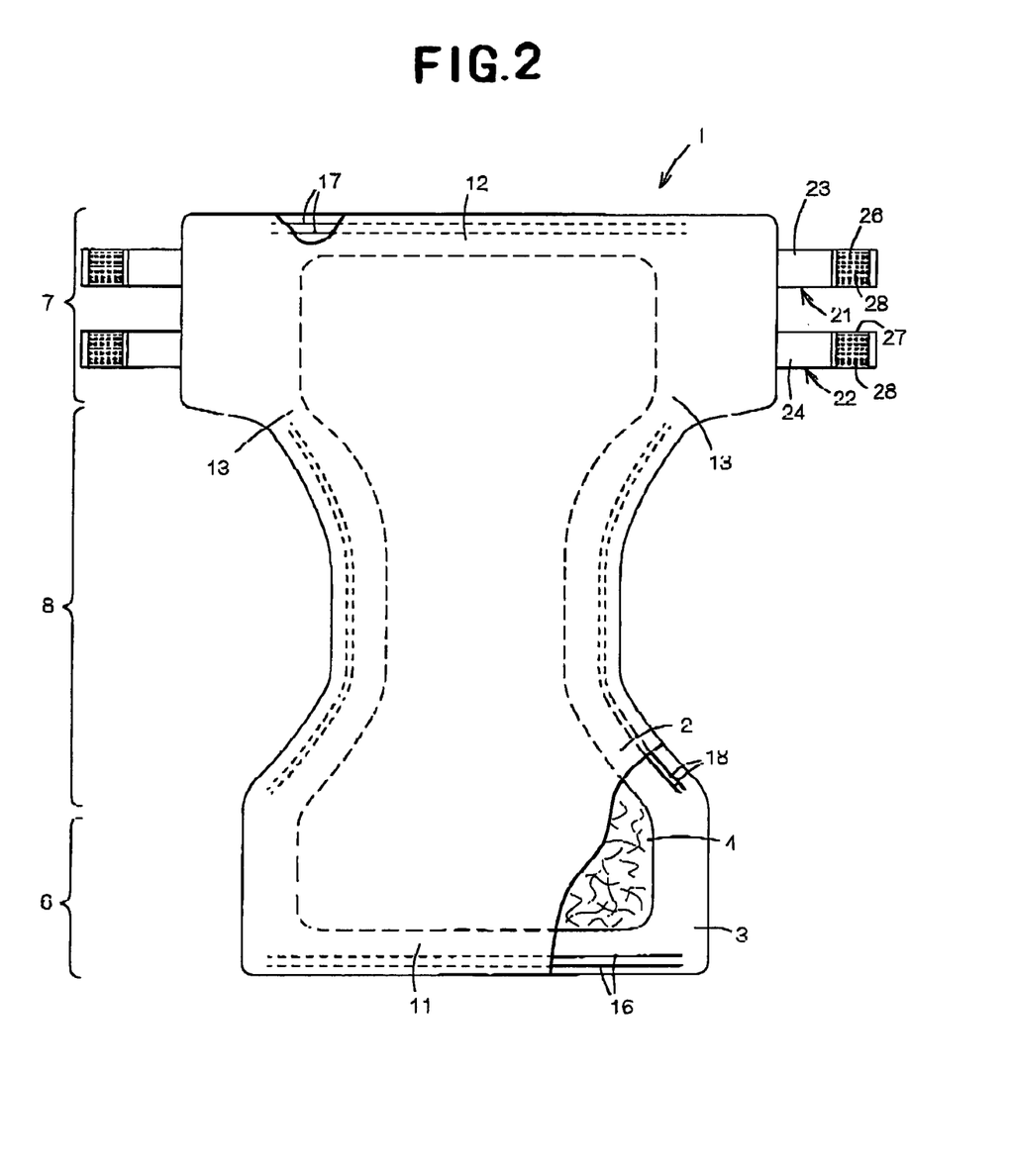
FIG. 2 is a partially cutaway plan view showing the disposable diaper in FIG. 1.

FIG. 1 is a side view showing the diaper 1 as put on a wearer's body and FIG. 2 is a partially cutaway plan view showing the diaper 1 of FIG. 1. The diaper 1 is an open-type one and comprises a liquid-pervious topsheet 2, a liquid-impervious backsheet 3 and a liquid-absorbent core 4 interposed between these two sheets 2, 3. The top- and backsheets 2, 3 extending outward beyond a peripheral edge of the core 4 are overlaid and joined together so as to form longitudinally opposite end flaps 11, 12 and transversely opposite side flaps 13. These flaps 11, 12, 13 are respectively provided with front waist elastic members 16, rear waist elastic members 17 and thigh-surrounding elastic members 18, all of which are bonded in a stretched state to respective inner surfaces of the top- and backsheets 2, 3. The diaper 1 is composed of, in a longitudinal direction, a front waist region 6, a rear waist region 7 and a crotch region 8 lying between these waist regions 6, 7. In the rear waist region 7, upper tape fasteners 21 and lower tape fasteners 22 extend outward from the respective side flaps 13 in a transverse direction orthogonal to the longitudinal direction of the diaper 1 as shown in FIG. 2 so that these tape fasteners 21, 22 may serve as means to connect the front and rear waist regions 6, 7 to each other. These two pairs of tape fasteners 21, 22 are made of elastomeric material, for example, an urethane rubber and respectively have upper and lower stretchable portions 23, 24 which are elastically stretchable in a transverse direction of the diaper 1 and upper and lower anchoring portions 26, 27 which are non-stretchable in the transverse direction of the diaper 1. The upper and lower stretchable portions 23, 24 are bonded to the outer surface of the backsheet 3 at proximal ends 23a, 24a, respectively and have distal ends being contiguous to the upper and lower anchoring portions 26, 27. While the upper and lower anchoring portions 26, 27 are provided on respective inner surface thereof with male members 28 of a mechanical fastener well known by the trade name of Magic Tape etc., respective distal ends of these anchoring portions 26, 27 are free from the male members 28 so as to be held easily. The front waist region 6 is provided on its outer surface with female members of the mechanical fasteners defining upper and lower target tape strips 31, 32 on which the respective upper and lower tape fasteners 21, 22 may be anchored in such a manner to he released.

These upper and lower tape fasteners 21, 22 are arranged so that the lower stretchable portions 24 of the lower tape fasteners 22 may have a stretch stress 1.2-2 times as great as that of the upper stretchable portions 23 of the upper tape fasteners 21 when the upper and lower tape fasteners 21, 22 are stretched by 30%, respectively. In wearing of the diaper 1 arranged in this manner, the lower tape fasteners 22 may be pulled with a relatively strong force to stretch the lower stretchable portions 24 and then anchored on the associated lower target tape strips 32 to put the diaper 1 in close contact tightly with the wearer's thighs and thereby to prevent leak of bodily discharges. On the other hand, the upper tape fasteners 21 may be pulled with a relatively weak force and then anchored on the associated upper target tape strips 31 to put the diaper 1 in close contact gently with the wearer's torso without a pressure on the wearer's torso.

Figure 3:
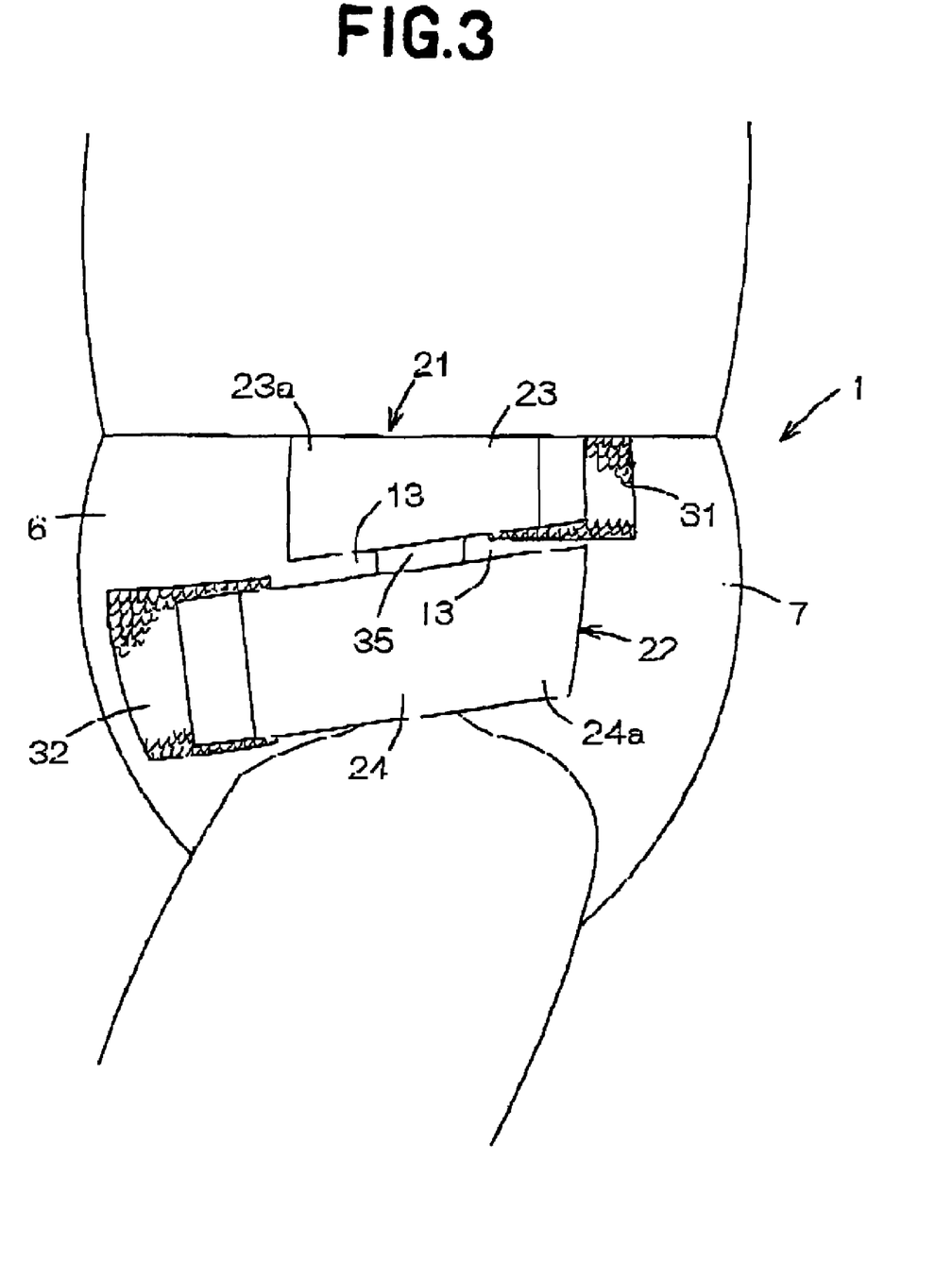
FIG. 3 is a view similar to FIG. 1 showing a preferred embodiment of this invention.
Figure 4:
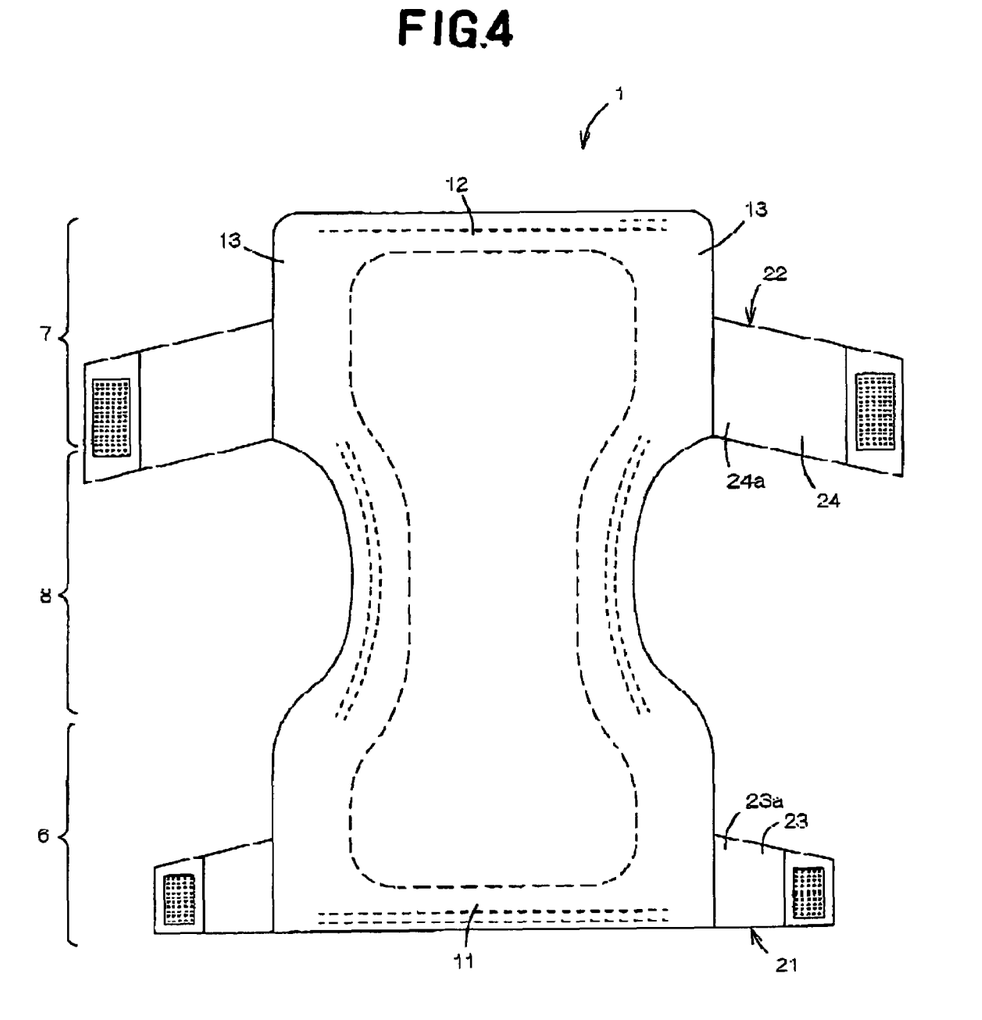
FIG. 4 is a view similar to FIG. 2 showing another preferred embodiment of this invention.

FIGS. 3 and 4 are views similar to FIGS. 1 and 2, respectively, showing another preferred embodiment of this invention. In this diaper 1, the upper tape fasteners 21 extend outward from the side flaps 13 in the front waist region 6 and the lower tape fasteners 22 extend outward from the side flaps 13 in the rear waist region 7. The rear waist region 7 of the diaper 1 is provided on its outer surface with the upper target tape strips 31 on which the upper tape fasteners 21 are anchored in such a manner to be released and the front waist region 6 of the diaper 1 is provided on its outer surface with the lower target tape strips 32 on which the lower tape fasteners 22 are anchored in such a manner to be released. The diaper arranged in this manner has the same function and effect as those has of the diaper 1 of FIGS. 1 and 2. In addition, while in the diaper 1 of FIGS. 1 and 2, it is possible for a baby wearing this diaper 1 to intentionally pull the upper tape fasteners 21, in the diaper 1 of FIGS. 3 and 4, it is impossible to do that. In the diaper 1 according to this embodiment also, the stretchable portions 24 have a stretch stress 1.2-2 times as great as that of the stretchable portions 23 when the upper and lower tape fasteners 21, 22 are stretched by 30%, respectively.

Figure 5:
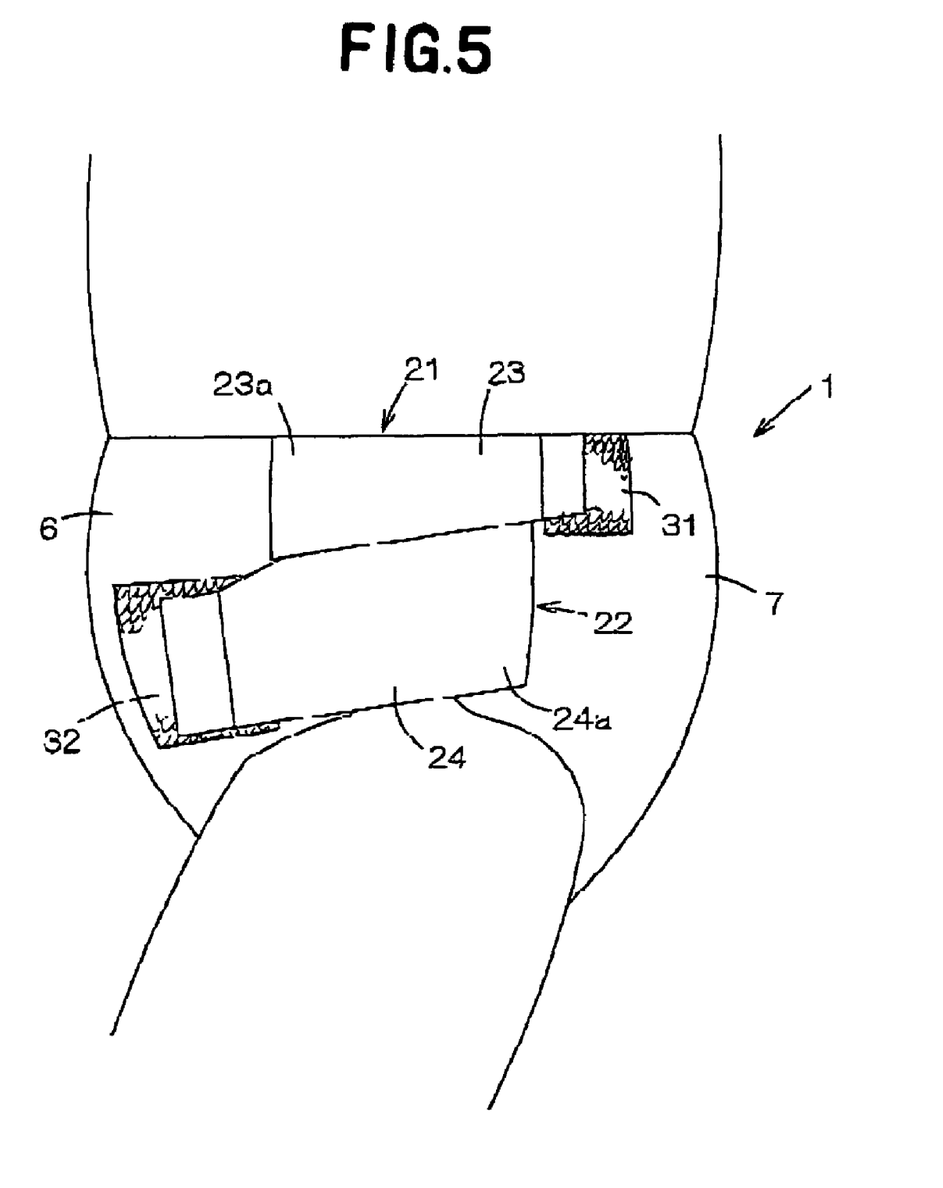
FIG. 5 is a view similar to FIG. 3 showing still another preferred embodiment of this invention.
Figure 6:
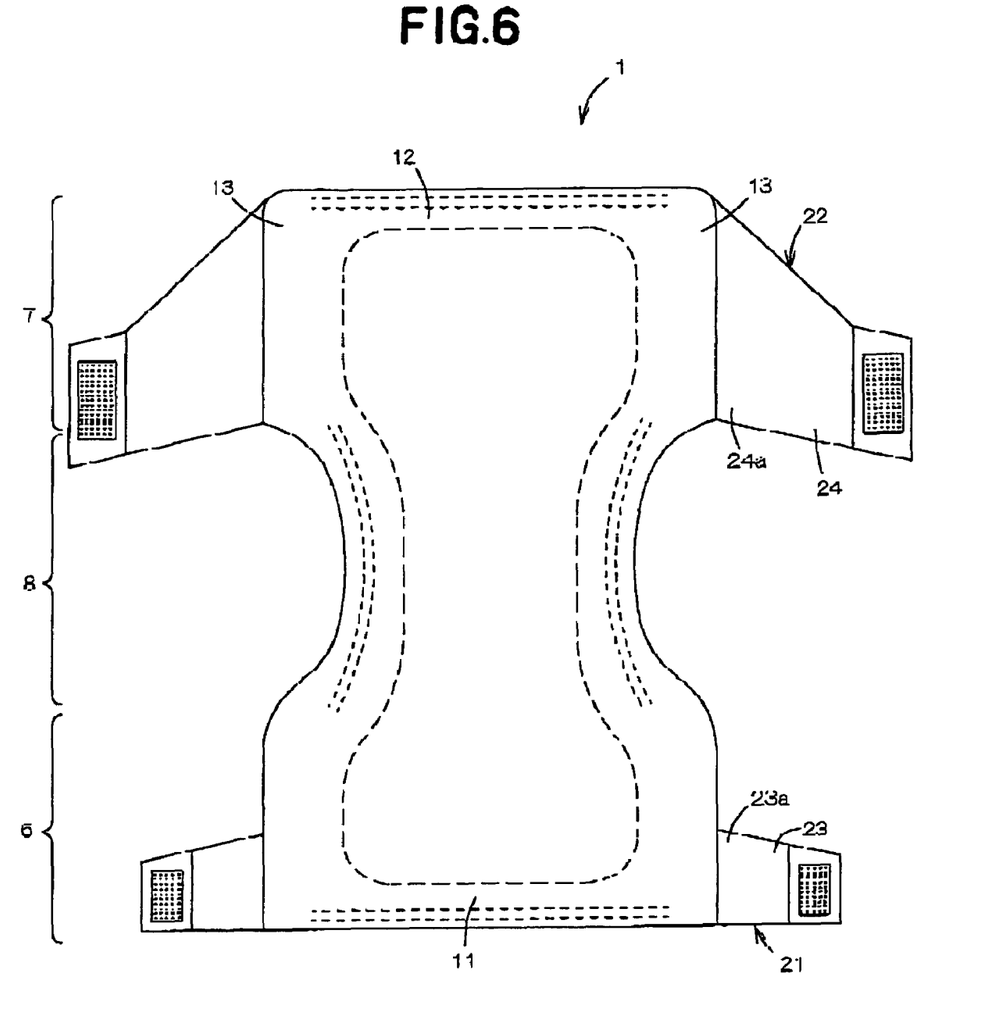
FIG. 6 is a view similar to FIG. 4 showing further another preferred embodiment of this invention.

FIGS. 5 and 6 are views similar to FIGS. 3 and 4, respectively, showing still another preferred embodiment of this invention. The diaper 1 according to this embodiment is distinguished from the diaper 1 of FIGS. 3 and 4 in that the proximal ends 24a of the lower tape fasteners 22 have a vertical dimension being substantially equal to a vertical dimension of the side flaps 13 in the rear waist region 7, i.e., larger than a vertical dimension of the proximal ends 24a of FIGS. 3 and 4. With this diaper 1, the lower tape fasteners 22 are first anchored on the respective lower target tape strips 32 in the front waist region 6 and then the upper tape fasteners 21 are anchored on the respective upper target tape strips 31 in the rear waist region 7. The upper and lower tape fasteners 21, 22 are partially overlaid so as not to form any gap 35 between the front and rear waist regions 6, 7 (See FIG. 3).

Without departing from the scope of this invention, the proximal ends 23a, 24a of the stretchable portions 23, 24 in the upper and lower tape fasteners 21, 22 may be formed from a non-stretchable material. It is also possible without departing from tho scope of this invention to use a Y-shaped tape for a stock material for these stretchable portions 23, 24 so that the proximal ends 23a, 24a thereof may be formed by inner and outer tape layers bonded to the inner and outer surfaces of the side flaps 13, respectively in the diaper 1. Such an arrangement ensures that these proximal ends 23a, 24a may be firmly attached to the side flaps 13. According to this invention, the dimensions of the upper and lower tape fasteners 21, 22 in a waist surrounding direction as well as in the vertical direction of the diaper 1 are not specified.

The disposable diaper according to this invention is primarily comprising two pairs of upper and lower connecting means, which are elastically stretchable and lying at the upper and lower portions of connected side edges, of which the upper connecting means have a relatively small stretch stress and the lower connecting means have a relatively great stretch stress. Such an arrangement ensures that the diaper may be put in close contact with the baby's, thighs tightly to prevent bodily discharges from leaking, on one hand, and the diaper may be put in close contact with the baby's torso gently without disturbing the wearer's abdominal breathing.

What is claimed is:

1. An open-type disposable diaper comprising: in a longitudinal direction, a front waist region, a rear waist region and a crotch region extending between these waist regions and contoured by transversely opposite side edge portions extending in said longitudinal direction and front and rear end portions extending in a transverse direction of said diaper orthogonal to said longitudinal direction, said side edge portions comprising opposite front side edge portions having a longitudinal length that extends from the crotch region to the front end portion and opposite rear side edge portions having a longitudinal length that extends from the crotch region to the rear end portion, said diaper further includes two pairs of releasable connecting means that extend transversely outward from the transversely opposite side edge portions in parallel to each other in said transverse direction and serving to connect said side edge portions of said front and rear waist regions together, said front and rear side edge portions being unconnected directly to one another along their entire longitudinal lengths and being indirectly connected to one another by said releasable connecting means which extend transversely outward from the transversely opposite side edge portions so as to define an open-type diaper, said two pairs of connecting means being elastically stretchable in said transverse direction, each of said two pairs of connecting means including a connecting means that lies at a lower portion of said side edge portions and a connection means that lies at an upper portion of said side edge portions, the connecting means lying on the lower portions of said side edge portions having a stretch stress that is greater than a stretch stress of said connecting means lying at said upper portions of said side edge portions, said pairs of connecting means being connected to and extending outward from the rear waist region.

2. The open-type disposable diaper according to claim 1, wherein said connecting means lying at said lower portions of said side edge portions have a stress that is 1.2-2 times as great as the stress of said connecting means lying at said upper portions of said side edge portions when said connecting means are stretched by 30%, respectively.

3. An open-type disposable diaper comprising: in a longitudinal direction, a front waist region, a rear waist region and a crotch region extending between these waist regions and contoured by transversely opposite side edge portions extending in said longitudinal direction and front and rear end portions extending in a transverse direction of said diaper orthogonal to said longitudinal direction, said side edge portions comprising opposite front side edge portions having a longitudinal length that extends from the crotch region to the front end portion and opposite rear side edge portions having a longitudinal length that extends from the crotch region to the rear end portion, said diaper further includes two pairs of connecting means extending in parallel to each other in said transverse direction, each connecting means having a fixed end and a free end by which free ends the connecting means can be used to removably connect said side edge portions of said front and rear waist regions together, said front and rear side edge portions being unconnected directly to one another along their entire longitudinal lengths and being indirectly connected to one another by said releasable connecting means which extend transversely outward from the transversely opposite side edge portions so as to define an open-type diaper, said two pairs of connecting means being elastically stretchable in said transverse direction, each of said two pairs of connecting means including a connecting means that lies at a lower portion of said side edge portions and a connection means that lies at an upper portion of said side edge portions, the connecting means lying on the lower portions of said side edge portions having a stretch stress that is greater than a stretch stress of said connecting means lying at said upper portions of said side edge portions.

4. The open-type disposable diaper according to claim 3, wherein said connecting means lying at said lower portions of said side edge portions have a stress that is 1.2-2 times as great as the stress of said connecting means lying at said upper portions of said side edge portions when said connecting means are stretched by 30%, respectively.

5. An open-type diaper according to claim 3, wherein said connecting means lying at said upper portions of said side edge portions extend outward from said side edge portions in said front waist region and are adapted to be anchored on said rear waist region in such a manner to be released and said connecting means lying at said lower portion of said side edge portions extend outward from said side edge portions in said rear waist region and are adapted to be anchored on said front waist region in such a manner to be released.

6. An open-type disposable diaper comprising: in a longitudinal direction, a front waist region, a rear waist region and a crotch region extending between these waist regions and contoured by transversely opposite side edge portions extending in said longitudinal direction and front and rear end portions extending in a transverse direction of said diaper orthogonal to said longitudinal direction, said diaper further includes two pairs of releasable connecting means that extend transversely outward from the transversely opposite side edge portions in parallel to each other in said transverse direction and serving to connect said side edge portions of said front and rear waist regions together, said side edge portions of said front and rear waist regions being unconnected directly to one another except by said releasable connecting means which extend transversely outward from the transversely opposite side edge portions so as to define an open-type diaper, said two pairs of connecting means being elastically stretchable in said transverse direction, each of said two pairs of connecting means including a pair of connecting means that extend transversely outward from one of the front and waist regions and a pair of connection means that extend transversely outward from the other of the front and waist regions.

7. An open-type disposable diaper according to claim 6, wherein one of the pair of connecting means that extends transversely outward from the front waist region and the a pair of connection means that extends transversely outward from the rear waist region is positioned closer to the crotch region than the other of the pair of connecting means.

8. An open-type disposable diaper according to claim 7, wherein the pair of connecting means that is closer to the crotch region has a stress that is 1.2-2 times as great as the stress of the other pair of connecting means when said connecting means are stretched by 30%, respectively.

\* \* \* \* \*

UNITED STATES PATENT AND TRADEMARK OFFICE
CERTIFICATE OF CORRECTION

PATENT NO. : 7,252,658 B2
APPLICATION NO. : 10/214222
DATED : August 7, 2007
INVENTOR(S) : Yasushi Sayama

It is certified that error appears in the above-identified patent and that said Letters Patent is hereby corrected as shown below:

On the title page
Add foreign priority data as follows:

Item [30]
Foreign Application Priority Data
Aug. 8, 2001 (JP) ....................... 2001-240273

Signed and Sealed this

Fourth Day of December, 2007

JON W. DUDAS
*Director of the United States Patent and Trademark Office*